United States Patent [19]

Borsanyi et al.

[11] Patent Number: 4,898,584
[45] Date of Patent: Feb. 6, 1990

[54] IMPLANTABLE PATIENT-ACTIVATED FLUID DELIVERY DEVICE

[75] Inventors: Alexander S. Borsanyi, Newport Beach; Russell J. Redmond, Goleta; Claude A. Vidal, Santa Barbara; Edmund E. Spaeth, Orange, all of Calif.

[73] Assignee: Baxter Healthcare Corporation, Deerfield, Ill.

[21] Appl. No.: 195,702

[22] Filed: May 18, 1988

[51] Int. Cl.$^4$ .............................................. A61M 1/00
[52] U.S. Cl. ..................................................... 604/153
[58] Field of Search ....................................... 604/8–10, 604/93, 116, 131, 151, 153, 175, 181–183, 185, 186, 244, 249, 246, 247, 891.1

[56] References Cited

U.S. PATENT DOCUMENTS

| | | |
|---|---|---|
| 3,769,982 | 11/1973 | Schulte . |
| 3,827,439 | 8/1974 | Schulte . |
| 4,013,074 | 3/1977 | Siposs . |
| 4,190,040 | 2/1980 | Schulte . |
| 4,193,397 | 3/1980 | Tucker . |
| 4,258,711 | 3/1981 | Tucker . |
| 4,265,241 | 5/1981 | Portner . |
| 4,360,019 | 11/1982 | Portner . |
| 4,400,169 | 8/1983 | Stephen . |
| 4,437,457 | 3/1984 | Trick . |
| 4,464,168 | 8/1984 | Redmond et al. ............... 604/9 |
| 4,487,603 | 12/1984 | Harris . |
| 4,496,343 | 1/1985 | Prosl . |
| 4,511,355 | 4/1985 | Franetzki . |
| 4,543,088 | 9/1985 | Bootman . |
| 4,544,371 | 10/1985 | Dormandy . |
| 4,548,607 | 10/1985 | Harris . |
| 4,557,722 | 12/1985 | Harris . |
| 4,560,375 | 12/1985 | Schulte . |
| 4,572,168 | 2/1986 | Fischell . |
| 4,588,394 | 5/1986 | Schulte et al. ............... 604/8 |
| 4,594,058 | 6/1986 | Fischell . |
| 4,604,090 | 8/1986 | Reinicke . |
| 4,626,244 | 12/1986 | Reinicke . |
| 4,627,832 | 12/1986 | Hooven . |
| 4,634,427 | 1/1987 | Hannula . |
| 4,639,244 | 1/1987 | Rizk . |
| 4,668,231 | 5/1987 | de Vries et al. ............... 604/153 |
| 4,699,615 | 10/1987 | Fischell et al. ............... 604/153 |

Primary Examiner—C. Fred Rosenbaum
Attorney, Agent, or Firm—Tilton, Fallon, Lungmus

[57] ABSTRACT

An implantable fluid delivery device for dispensing metered aliquots of liquid medication upon finger-pressure activation of the device by a patient. The device includes a soft, deformable needle-piercable casing having a fluid reservoir in which is located a relatively-rigid, apertured support plate that divides the reservoir into upper and lower chambers. A compressible, positive displacement pump chamber or housing is mounted upon the plate within the upper chamber and includes passages communicating with both the lower chamber and an outlet port. Force applied to a central target zone of the top wall causes compression of the pump housing and delivery through the outlet port of an amount of fluid equal to the displacement of the pump housing. The same target zone of the top wall serves as a self-sealing injection site for replenishing the fluid supply of the reservoir. A rigid, protective needle guard is disposed within the upper chamber above the pump housing to shield that housing against contact by an injection needle when the fluid supply is being replenished. The rigid plate that supports the pump housing also distributes applied pumping forces and provides a platform for supporting other elements of the device, including a fluid filter and surge protector located in the lower chamber of the reservoir at the inlet to the pump housing.

15 Claims, 3 Drawing Sheets

IMPLANTABLE PATIENT-ACTIVATED FLUID DELIVERY DEVICE

BACKGROUND OF THE INVENTION

Various implantable devices have been disclosed in the prior art that may be activated by ambulatory patients when the administration of measured doses of therapeutic agents is required. For example, cancer patients suffering from terminal lower torso cancer may require routine injections of morphine, either epidurally or intrathecally, and, upon receiving such injections, are sufficiently relieved of the symptoms of pain to move about and perform many routine and normal functions. Other chronic ailments also require frequent dosages of therapeutic agents in the treatment of chronic conditions, such as insulin in the case of diabetes. Implantable devices capable of delivering measured amounts of medicament on demand are disclosed in U.S. Pat. Nos. 4,634,427, 4,548,607, 4,588,394, 4,557,722, 4,544,371, and 4,543,088. Other U.S. patents of general interest pertaining to implantable pumping or infusing systems are U.S. Pat. Nos. 4,560,375, 4,258,711, 3,769,982, 3,827,439, 4,013,074, 4,265,241, 4,360,019, 4,487,603, 4,496,343, 4,511,355, 4,604,090, and 4,627,832. Reference may also be had to U.S. Statutory Invention Registration H150.

SUMMARY OF THE INVENTION

Despite the attention that has been directed in recent years to the development of implantable drug delivery systems, prior devices have often been deficient in significant respects. The recognition of such deficiencies is considered to be one of the important aspects of this invention, along with the discovery and development of the means for overcoming those shortcomings. Unlike many of the prior devices, the fluid delivery device of this invention is formed of soft and deformable (preferably elastomeric) material capable of being worn comfortably and effectively in implanted condition over an extended period. In spite of its compliant outer casing, the device has a relatively rigid internal structure that serves to support various operative elements, such support also performing the functions of distributing pumping forces produced by finger pressure and protecting the casing (as well as interior elements) against damage and possible leakage during refilling operations.

The compactness of the device and its ease of operation result partly from the fact that its top wall has a central target zone that may be easily located by touch (even when the device is implanted) and that serves as both the pump-actuating site against which finger pressure is exerted when drug delivery is needed and as the site for medicament injection when refilling of the reservoir is required. Enhanced self-sealing properties of the top wall and its underlying structure, coupled with a relatively rigid protective shield interposed between the top wall and the pump assembly, helps insure that the device may be easily refilled without risk of internal damage or leakage.

Even though the soft, resilient casing of the device yields or deforms with body movements and in response to both internally and externally applied forces, fluid pressure equalization within the device insures that pump activation and drug delivery do not occur unless directed and localized force is applied specifically to the target zone—a force that can be expected to be applied only intentionally.

In brief, the implantable fluid delivery device includes a casing formed of soft, deformable polymeric material, preferably elastomeric material, having top and bottom walls defining a fluid reservoir therebetween. A rigid support plate is disposed within the casing and divides the reservoir into upper and lower chambers that communicate with each other through an opening in the plate. Compressible pumping means is mounted upon the plate within the upper chamber and includes a deformable pump housing that defines a pump cavity or chamber with a first passage connecting that cavity with the lower chamber of the reservoir. A second passage connects the same cavity with the outlet port of the device, and inlet and outlet check valves are positioned to control flow through the respective passages.

The top wall of the casing includes a flexible pump-actuating zone. Connecting means in the form of a self-sealing septum combined with a rigid cover plate operatively connect the top wall's pump actuating zone with the pump housing. The self-sealing properties of the piercable septum are enhanced by a construction that maintains that septum in a partially-compressed state. Although the casing and many of the components contained within it are readily deformable, being formed of silicone rubber or other suitable material, and although build up of fluid pressure due to unexpected compressive loads on the device is possible, pressure equalization within the reservoir, on opposite sides of elements such as the deformable pump housing and the check valve for the second passage, insure that deformation of the casing will not result in fluid delivery unless such deformation specifically includes depression of the target zone of the top wall in the direction of the compressible pump.

A porous metal filter is mounted upon the support plate at the entry to the first passage leading from the reservoir to the pump cavity. In addition to filtering fluid, the filter also performs a rate controlling function and therefore prevents surges of fluid, produced by compressive deformation of the device's deformable casing, that might otherwise cause damage to the pump assembly. Channel-defining ribs within the reservoir also function to equalize pressure within that reservoir and prevent obstructive contact with the rigid filter that might block fluid flow to the pump cavity.

Other features, objects, and advantages will become apparent from the specification and drawings.

DRAWINGS

DETAILED DESCRIPTION OF PREFERRED EMBODIMENT

Figure 2:
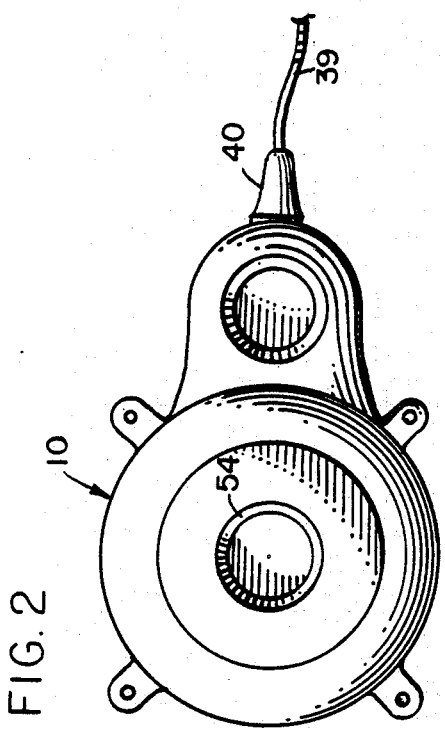
FIG. 2 is a top plan view.
Figure 1:
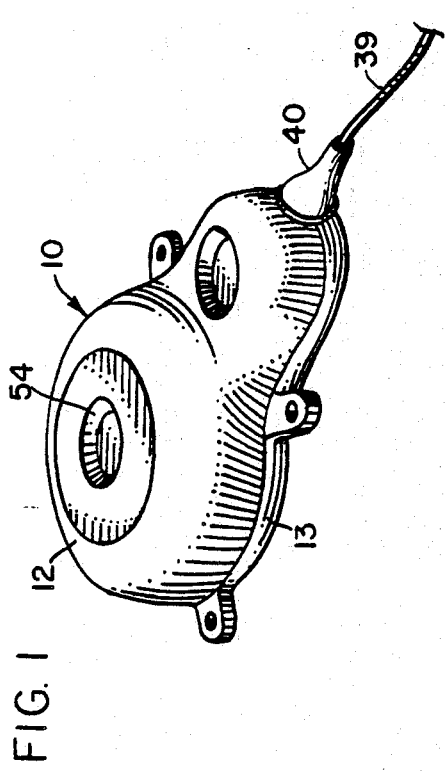
FIG. 1 is a perspective view of an implantable fluid delivery device embodying this invention.
Figure 3:
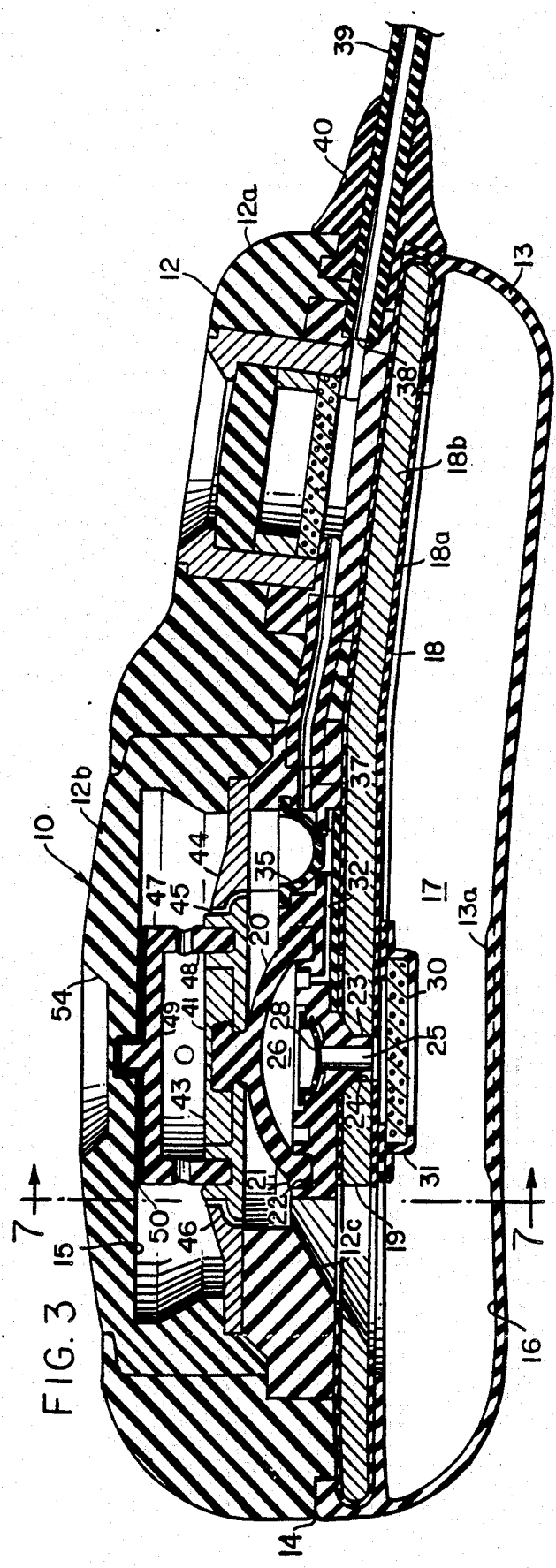
FIG. 3 is an enlarged longitudinal vertical sectional view of the device.

Referring to the drawings, and particularly to FIGS. 1-3, the numeral 10 generally designates an implantable delivery device having a casing 11 formed of soft, deformable polymeric material. While various materials having such properties might be used, an elastomeric material such as silicone rubber has been found particularly effective because of its deformability, recoverability, durability, and biocompatability. Viewed generally, the casing includes preformed (molded) upper and lower walls 12 and 13 that are sealed together along a horizontal midline 14. To facilitate manufacture, the upper wall 12 may be formed in two or more sections that allow the prefabrication of subassemblies. Thus, in the illustration given, upper wall 12 includes main section 12a, central section 12b, and inner section 12c. The central and inner sections together define an upper chamber 15, whereas the bottom wall defines a lower chamber 16. The two chambers communicate and together define an enlarged reservoir 17.

Figure 7:
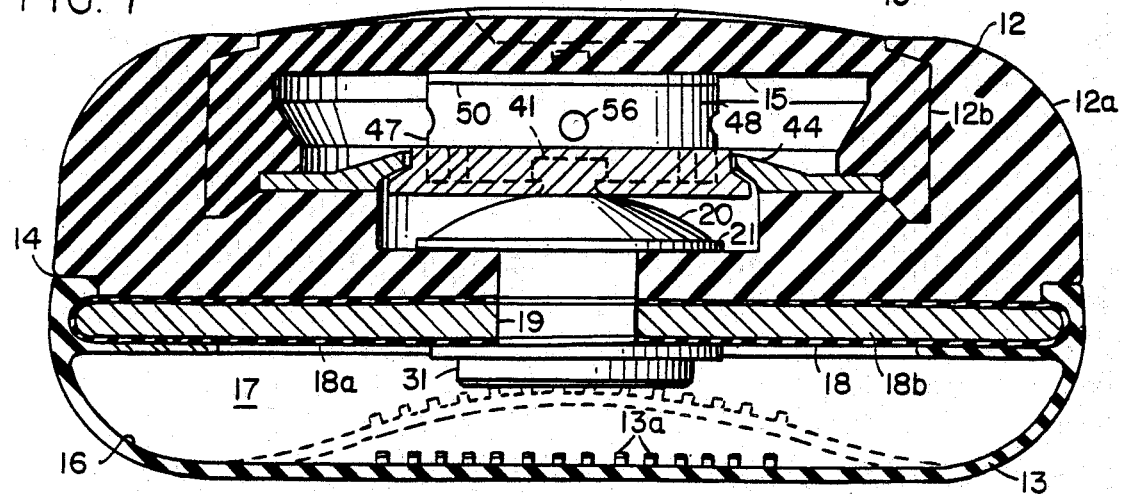
FIG. 7 is a transverse sectional view taken along line 7—7 of FIG. 3.

A relatively rigid support plate 18 is interposed between the upper and lower chambers of the reservoir and, as shown most clearly in FIGS. 3 and 7, extends substantially the full width and length of the casing. The plate is sandwiched between the upper and lower walls 12 and 13 and, if desired, may be provided with an outer layer 18a of silicone rubber or other suitable material to enhance biocompatability and facilitate adhesive attachment of the parts. The core 18b of the support plate may be formed of any tough and rigid material, including metallic and ceramic materials, although a polymeric material such as polycarbonate is believed particularly suitable. Opening 19 through the support plate 18 places the upper and lower chambers 15, 16 of the reservoir in communication with each other. In use of the device, at least the lower chamber of the reservoir would contain a liquid medicament to be discharged in metered amounts upon actuation of the device; however, for clarity of illustration such fluid is not depicted in the drawings.

The pumping means for the device is located in the upper chamber 15 of the reservoir and is supported upon plate 18. The pumping means includes a dome-shaped pump housing 20 formed of silicone rubber or other suitable elastomeric material. The rim 21 of the pump housing is secured within an annular channel 22 provided in the upper surface of inner wall section 12c, and a downwardly-projecting stem portion 23 of that wall section projects through an opening 24 in the rigid support plate. Inlet flow passage 25 extends through the stem portion 23 and places the pump chamber or cavity 26 in communication with the lower chamber 16 of the reservoir. An annular valve seat 27 is provided at the upper end of passage 25 and is normally engaged by a dish-shaped elastomeric membrane valve member 28 that has its circular outer peripheral portion secured to wall section 12c. Like other components of the drug delivery device, the membrane valve member 27 may be formed of silicone rubber. As shown most clearly in FIGS. 4-6, the valve member is provided with openings 29 therethrough that are located outboard of valve seat 27 and that therefore allow flow of fluid between passage 25 and pump chamber 26 only when the valve member 28 is urged away from valve seat 27.

Directly below the pump, and mounted along the underside of the support plate 18, is a rigid filter member or disc 30. The disc may be formed of sintered metal or a fine metallic mesh and is secured in place by an annular rim 31 adhesively bonded to the underside of the support plate 18 about the entrance to inlet passage 25. Directly below the filter disc 30, the surface of the bottom wall of the casing is provided with parallel ribs 13a that prevent the bottom wall from blocking fluid flow from lower chamber 16 into filter 30 and inlet passage 25 should the bottom wall be flexed upwardly into contact with the filter (FIG. 7).

Figure 5:
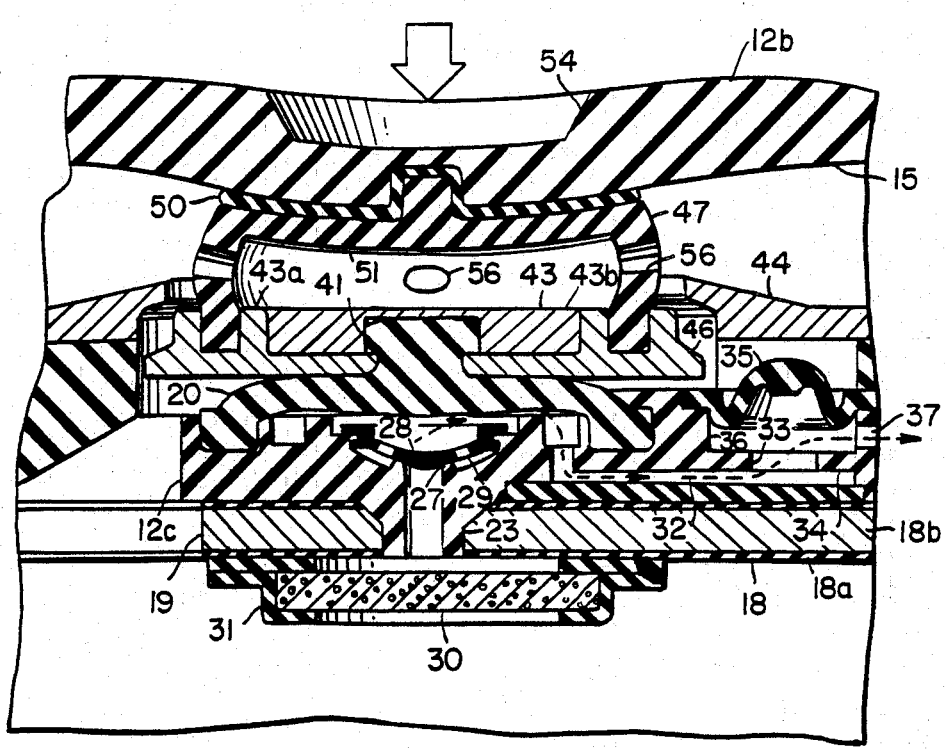
FIG. 5 is a fragmentary sectional view similar to FIG. 4 but illustrating the condition of the device during a pumping step.

A second passage 32 also communicates with the chamber 26 of the pump and leads radially away from the pump through the inner section 12c of the top wall. The second passage 32 is parallel and in close proximity to rigid support plate 18 and communicates at its opposite end with a valve opening 33 defined by an annular flexible lip 34 that is preferably formed integrally with section 12c of the top wall. The lip defines a valve seat and the opening 33 is normally closed by a cup-shaped elastomeric valve member 35 mounted within cylindrical chamber 36. In its normal undeformed state, valve member 35 engages lip 34 to maintain the valve in closed condition; however, as shown in FIG. 5, the valve member is capable of being deformed upwardly into unseated condition to allow fluid flow from secondary passage 32 and opening 33 into chamber 36 and then into outlet passage 37. The outlet passage leads to outlet port 38 which in turn communicates with the lumen of a catheter 39. A tapered ferrule or connector 40 is secured to the casing 11 and supports the catheter at its point of exit from the casing.

All of the elements so far described, except for filter disc 30 and the core 18b of support plate 18, are composed of soft, deformable material. Silicone rubber of the same formulation or different formulations may be used for all of such resilient elements which, as already indicated, are secured together by any suitable adhesive to provide the assembly illustrated in the drawings.

The dome-shaped pump housing 20 has an upstanding stem portion 41 that is anchored to a rigid disc 43 formed of polycarbonate or any other suitable material having sufficient strength, hardness, and rigidity to resist needle penetration. In the illustration given, the disc 43 is formed in two sections 43a and 43b to facilitate assembly, or subassembly, with pump housing 20; however, it is to be understood that if desired the rigid disc 43 may instead be formed in one piece.

Figure 4:
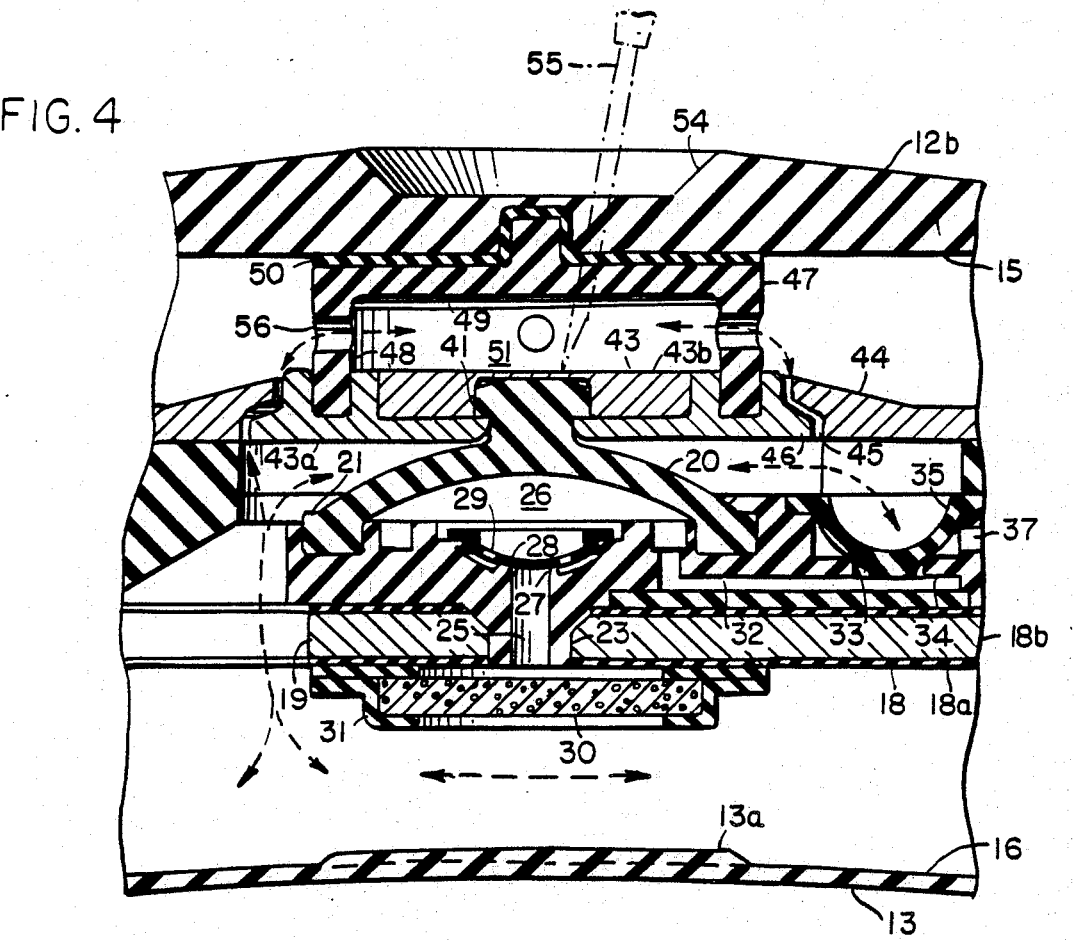
FIG. 4 is a still further enlarged vertical longitudinal sectional view showing the filling port, needle guard, and pump assembly.

The disc 43 is surrounded by an annular plate 44 that is also formed of rigid material, preferably the same material as disc 43. The periphery of the annular plate is locked in place between the central section 12b and the inner section 12c of upper wall 12. As shown in FIGS. 3 and 4, the opposing edges or side surfaces of the disc 43 and annular plate 44 are spaced apart to provide flow passages 45 that maintain the portions of the upper chamber above and below the disc and annular plate in pressure-equalizing flow relation. A rim 46 of the disc 43 projects outwardly and is engagable with the annular plate 44 to limit the extent of upward movement of the disc and, if desired, the rim may be serrated or discontinuous to insure that passages 45 remain open at all times.

Above disc 43 is an inverted cup-shaped septum 47 having an apertured side wall 48 and, when fully assembled, a planar end wall 49. The lower periphery of the side wall 48 is secured within an annular channel provided in rigid disc 43. The septum is formed of an elastomer such as silicone rubber and is secured to the underside of the central section 12b of the casing's top wall 12 by means of an adhesive attachment layer 50.

Figure 8:
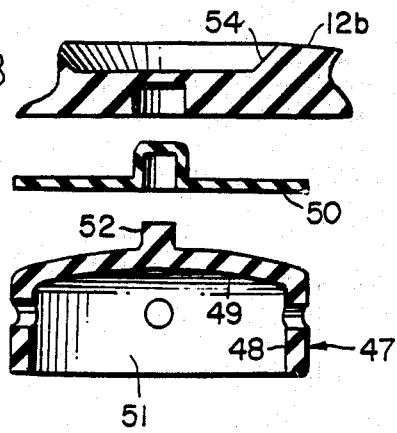
FIG. 8 is an exploded sectional view illustrating the deformable septum and associated parts prior to assembly.
Figure 9:
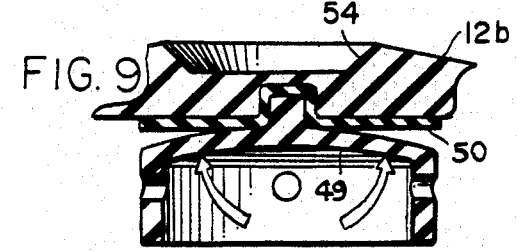
FIG. 9 is a sectional view illustrating the parts of FIG. 8 in partially assembled condition.

Of particular importance is the fact that end wall 49 of the elastomeric septum is spaced well above disc 43 to define a medicament-receiving chamber 51. Also, while shown in the assembly drawings to be of generally planar configuration (except for locating protuberance 52), the end wall in an untensioned state is dome shaped. As shown in FIG. 8, in the absence of distorting forces the convex end wall 49 curves upwardly and inwardly so that when flattened and adhesively secured to the planar undersurface of the casing's top wall section 12b, the end wall 49 will have its upper surface portion in a compressed state and will be maintained in that compressed state by adhesive layer or pad 50. It has been found that such limited compression of the upper stratum of end wall 49 greatly enhances the self-sealing properties of the septum upon withdrawal of an injection needle.

Ideally, the upper surface of the central section 12b of casing's top wall 12 is provided with an indentation 54 of circular outline. The indentation identifies the target site for both pump actuation and fluid injection and helps a user locate such site by touch even when the fluid delivery device is implanted. When fluid is to be supplied to the reservoir, the needle 55 of a syringe is simply inserted into the casing through the indented zone of the top wall until the tip of the needle engages rigid disc 43 within medicament-receiving chamber 51 (FIG. 4). Discharge of fluid from the syringe flows outwardly through openings 56 in the side wall of septum 47. Since the upper and lower chambers of the reservoir are in communication, such fluid enters the space above the dome-shaped pump housing 20 and above outlet valve member 35, and is free to pass into the lower chamber through opening 19. Upon removal of needle 55, the compressed end wall 49 of the septum 47 then closes and reseals the reservoir.

Figure 6:
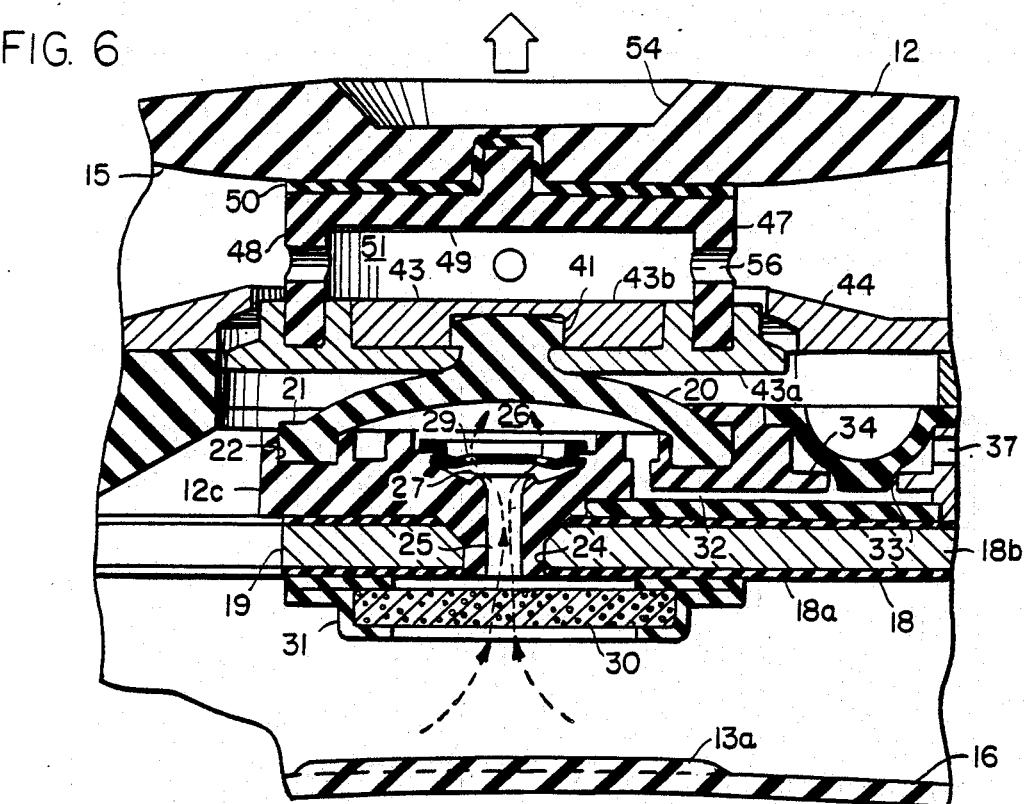
FIG. 6 is a similar fragmentary sectional view showing the parts during a recovery step in which the pump cavity is being refilled.

The same target zone, as defined by indentation 54, is used for finger actuation of the pump mechanism. Depression of the top wall 12 in the area of indentation 54, as depicted in FIG. 5, drives the septum 47 and rigid disc 43 downwardly, deforming pump housing 20 and substantially exhausting pump cavity 26. Fluid in the pump cavity is driven outwardly into second passage 32 with the pressure increase beneath outlet valve 35 causing the outlet valve to flex upwardly into open position. An aliquot of fluid substantially equal to the volume of pump chamber or cavity 26 (when the pump housing is undeformed) is therefore discharged into the outlet passage 37 and through outlet port 38. When finger pressure is removed, the top wall returns to its original position largely because of the recovery forces exerted by the dome-shaped pump housing 20 and the flexible top wall portion 12b. As the pump cavity 26 expands, the pressure differential causes the membrane valve member 28 to lift away from its seat 27, allowing fluid from the lower chamber 16 of the reservoir to enter the pump cavity 26 through the first passage 25 and openings 29 in the membrane (FIG. 6). Once the pump cavity is filled and pressure is equalized, the inlet valve member 28 closes and the parts again assume the relationships depicted in FIGS. 3 and 4.

Since the upper and lower chambers of the reservoir are in open communication at all times, deformations of the resilient casing 11 produced by body movement or other causes do not result in unintentional delivery of medicament to the patient. For example, should patient movement cause compression of the device and subsequent upward flexure of bottom wall 13 from the position shown in FIG. 4, fluid displaced from lower chamber 16 is free to enter the upper chamber of the reservoir, including the area directly above outlet valve member 35. The outlet valve will therefore remain closed despite the deformation of the casing because pressure will be equal on both sides of outlet valve 35. The double-headed arrows in FIG. 4 are intended to indicate the reversibility of movement of fluid throughout the upper and lower chambers of the reservoir that results in pressure equalization.

While in the foregoing, an embodiment of the invention has been disclosed in considerable detail for purposes of illustration, it will be understood by those skilled in the art that many of these details may be varied without departing from the spirit and scope of the invention.

We claim:

1. An implantable, patient-activated device for dispensing metered amounts of fluid to a patient, comprising a casing formed of soft, deformable polymeric material having a top wall and a bottom wall defining a fluid reservoir with an outlet port; a rigid support plate within said casing dividing said reservoir into upper and lower chambers and having an opening therethrough placing said chambers in communication with each other; pumping means mounted upon said plate within said upper chamber and comprising a compressible pump housing defining a pump cavity; first passage-providing means defining an inlet passage extending from said lower chamber to said cavity; inlet check valve means along said inlet passage; second passage-providing means defining an outlet passing extending from said cavity to said outlet port; outlet check valve means along said outlet passage; said top wall having a flexible pump-actuating zone; and connecting means within said upper chamber connecting said pump-actuating zone and said pump housing so that when said pump-actuating zone is depressed said pump housing is compressed to discharge from said outlet port an amount of fluid substantially equal to the volume of said pump cavity; said pump-actuating zone of said top wall being piercable by an injection needle and said pump-actuating zone also functioning as a target zone for the injection of fluid into said reservoir; and barrier means within said upper chamber for shielding said pump housing against contact by an injection needle inserted through said target zone; said barrier means including a rigid, needle-impenetrable disc connected to and extending over said pump housing.

2. The device of claim 1 in which said barrier means also includes a rigid, needle-impenetrable plate supported by said top wall within said upper chamber and extending about said disc when said pump housing is uncompressed.

3. The device of claim 1 in which said connecting means includes a needle-penetrable self-sealing pump septum between said pump-actuating zone of said top wall and said disc.

4. The device of claim 3 in which said pump septum is of inverted cup-shaped configuration having an apertured side wall and an end wall; said end wall being secured to said top wall in a state of radial compression.

5. The device of claim 4 in which said end wall is maintained by said top wall in substantially planar condition but is dome-shaped in configuration in an uncompressed state.

6. The device of claim 5 wherein an adhesive layer adhesively secures said end wall and said top wall together.

7. The device of claim 1 in which said top wall has an outer surface provided with an indentation indicating the location of said pump-actuating zone.

8. The device of claim 1 in which said rigid support plate extends substantially the entire length and width of said casing.

9. The device of claim 1 in which said first passage-providing means defines an entrance to said inlet passage in said lower chamber; and a rigid, porous filter member disposed within said lower chamber at said entrance to said inlet passage.

10. The device of claim 9 in which said rigid filter member is secured to said rigid support plate.

11. The device of claim 1 in which said outlet check valve means is supported by said support plate in laterally-spaced relation with respect to said pump housing.

12. The device of claim 11 in which said outlet check valve means is disposed in said upper chamber of said reservoir.

13. The device of claim 11 in which said outlet check valve means includes an annular valve seat defining a valve opening and a flexible membrane valve member engagable with said seat; said membrane valve member having one surface exposed to fluid pressure within said outlet passage and an opposite surface exposed to fluid pressure within said reservoir, assuring pressure equilibrium when said pumping means is not activated.

14. The device of claim 1 in which said deformable polymeric material is elastomeric.

15. The device of claim 14 in which said polymeric material is silicone rubber.

* * * * *